(12) United States Patent
Bitter et al.

(10) Patent No.: US 8,217,353 B1
(45) Date of Patent: Jul. 10, 2012

(54) NON-ASTIGMATIC IMAGING WITH MATCHED PAIRS OF SPHERICALLY BENT REFLECTORS

(75) Inventors: Manfred Ludwig Bitter, Princeton, NJ (US); Kenneth Wayne Hill, Plainsboro, NJ (US); Steven Douglas Scott, Wellesley, MA (US); Russell Feder, Newton, PA (US); Jinseok Ko, Cambridge, MA (US); John E. Rice, N. Billerica, MA (US); Alexander Charles Ince-Cushman, New York, NY (US); Frank Jones, Manalapan, NJ (US)

(73) Assignee: U.S. Department of Energy, Washington, DC (US)

( * ) Notice: Subject to any disclaimer, the term of this patent is extended or adjusted under 35 U.S.C. 154(b) by 680 days.

(21) Appl. No.: 12/436,708

(22) Filed: May 6, 2009

(51) Int. Cl.
*G01J 1/00* (2006.01)
(52) U.S. Cl. .................................................. 250/336.1
(58) Field of Classification Search ................ 250/336.1
See application file for complete search history.

(56) References Cited

U.S. PATENT DOCUMENTS

| | | | | |
|---|---|---|---|---|
| 3,624,395 A | * | 11/1971 | Togel et al. ...................... | 378/82 |
| 5,016,265 A | * | 5/1991 | Hoover ............................ | 378/43 |
| 5,026,131 A | * | 6/1991 | Jannson et al. ................. | 359/15 |
| 5,581,639 A | * | 12/1996 | Davies et al. ................... | 385/10 |
| 6,259,763 B1 | * | 7/2001 | Bitter et al. .................... | 378/82 |
| 2009/0225947 A1 | * | 9/2009 | MacDonald et al. ........... | 378/85 |

OTHER PUBLICATIONS

Bergmann et al., "High-resolution X-ray imaging using Rowland-circle Bragg optics," 2002, IEEE Nuclear Science Symposium Conference Record, vol. 3, pp. 1481-1483.*
Wittry et al., "X-ray optics of diffractors curved to a logarithmic spiral," 1993, Journal of Applied Physics, Volo. 74, pp. 3534-3540.*
Bitter et al., "Wide-angle point-to-point x-ray imaging with almost arbitrarily large angles of incidence," 2008, Review of Scientific Instruments, vol. 79, pp. 10E927-1 to 10E927-3.*

* cited by examiner

*Primary Examiner* — Kiho Kim
(74) *Attorney, Agent, or Firm* — Bradley W. Smith; Daniel Park; John T. Lucas (57) ABSTRACT

Arrangements for the point-to-point imaging of a broad spectrum of electromagnetic radiation and ultrasound at large angles of incidence employ matched pairs of spherically bent reflectors to eliminate astigmatic imaging errors. Matched pairs of spherically bent crystals or spherically bent multilayers are used for X-rays and EUV radiation; and matched pairs of spherically bent mirrors that are appropriate for the type of radiation are used with microwaves, infrared and visible light, or ultrasound. The arrangements encompass the two cases, where the Bragg angle—the complement to the angle of incidence in optics—is between 45° and 90° on both crystals/mirrors or between 0° and 45° on the first crystal/mirror and between 45° and 90° on the second crystal/mirror, where the angles of convergence and divergence are equal. For x-rays and EUV radiation, also the Bragg condition is satisfied on both spherically bent crystals/multi-layers.

7 Claims, 4 Drawing Sheets

NON-ASTIGMATIC IMAGING WITH MATCHED PAIRS OF SPHERICALLY BENT REFLECTORS

The United States Government has rights in this invention pursuant to Contract No. DE-AC02-76CH03073 with the U.S. Department of Energy.

FIELD OF THE INVENTION

This invention relates to imaging apparatus for use with electromagnetic radiation of virtually any wavelength and the imaging with ultrasound.

BACKGROUND OF THE INVENTION

Figure 1:
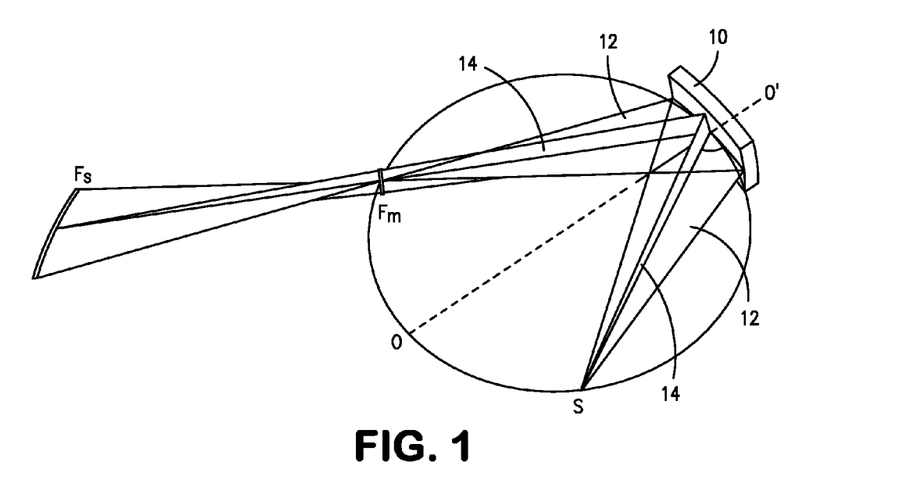
FIG. 1 is a simplified schematic diagram of the astigmatic imaging errors of a prior art imaging arrangement using a spherical reflector and a point source on the Rowland circle of the reflector.

U.S. Pat. No. 6,259,763 discloses a high-resolution x-ray imaging crystal spectrometer to record spatially resolved impurity line spectra emitted from tokamaks and other extended plasma sources, used in magnetic confinement nuclear fusion energy research, for Doppler measurements of ion temperature and toroidal plasma rotation velocity profiles. The spectrometer concept is based on the Johann configuration, but the typically used cylindrically bent crystal and one-dimensional, position-sensitive detector are replaced by a spherically bent crystal and a two-dimensional, position sensitive detector, whereby spatial resolution or 1d-imaging is obtained in a direction perpendicular to the main diffraction plane. The imaging properties of this spectrometer, which are schematically depicted in FIG. 1, are determined by the astigmatism of a spherical reflector, such as a crystal or minor, 10, due to the fact that the images formed by the sagittal and meridional rays 12 and 14 emanating from a point source on the minor's Rowland circle 16 are spatially separated and mutually perpendicular lines at $F_s$ and $F_m$. Thus, by reversing the rays in FIG. 1, we see that photons, which seem to emanate from the sagittal line image $F_s$, are being focused to a point on the Rowland circle. The possibility of obtaining spatially resolved spectra follows immediately from the rotational symmetry of the ray pattern about the normal 00' of the spherically bent crystal 10, since by a rotation about this normal the point source (or point image) S and the associated sagittal line image (or line source) $F_s$ move on a cone in opposite directions above and below the main diffraction plane, so that different points on the detector correspond to different locations in the plasma. On tokamaks, the preferred experimental arrangement is such that the main diffraction plane coincides with the horizontal mid-plane, so that the sagittal line image (line source) $F_s$ is parallel to the toroidal magnetic field, along which the electron density, electron temperature, and therefore the x-ray emissivity are uniform. Spatial resolution and 1d-imaging of tokamak plasmas is thus obtained perpendicular to the toroidal magnetic field. This 1d-imaging scheme has been successfully used for the diagnosis of (extended) tokamak plasmas on NSTX and Alcator C-Mod, where, with the proper experimental arrangement, the astigmatism of a spherical mirror or crystal is not a matter of concern. This imaging scheme is, however, not readily applicable to other plasma sources, where a direction of symmetry or uniform x-ray emission is not provided. In such cases, other optical systems, with near paraxial rays, i.e., restricted optical apertures and small angles of incidence, are most commonly used to avoid astigmatism. Although, variants of the optical scheme shown in FIG. 1 are also used in the diagnosis of laser-produced plasmas and Z-pinch plasmas. But the images obtained with a single spherically bent crystal from such sources are, in principle, not sharp and flawed by astigmatic errors even if the highest, still practicable, Bragg angles of 80° are used, so that these images are not fully satisfactory for a detailed data analysis.

OBJECTS AND SUMMARY OF THE INVENTION

Accordingly, it is an object of the present invention to provide an imaging arrangement for use over a broad spectrum of electromagnetic radiation capable of eliminating image distortions due to astigmatism.

It is another object of the present invention to provide an imaging arrangement capable of accommodating electromagnetic radiation at large angles of incidence without introducing image distortions arising from astigmatism.

Yet another object of the present invention is to provide a spectrometer particularly adapted for use in studying and analyzing hot plasmas which, by providing an indirect view of the plasma, is not subject to damage or destruction by debris emitted from the plasma source.

A further object of the present invention is to provide an electromagnetic radiation imaging arrangement which allows wide-angle, point-to-point radiation imaging with large angles of incidence without image astigmatism distortion.

A still further object of the present invention is to provide non-astigmatic imaging using a matched pair of spherically bent crystals which is particularly adapted for use in the analysis of hot plasmas, the imaging of biological samples, the observation of spectra of materials such as helium-like argon, and the use of spherically bent multi-layer structures for EUV lithography.

A still further object of the present invention is to provide non-astigmatic imaging with spherically bent reflectors for the imaging with ultrasound, which is particularly adapted for imaging applications in medicine as well as imaging and focusing of high intensities of ultrasound for military applications.

A still further object of the present invention is to provide an electromagnetic radiation imaging arrangement which allows for non-co-planar, point-to-point radiation imaging at large angles of incidence without astigmatism.

Yet another object of the present invention is to provide a two mirror imaging arrangement capable of providing good focusing for incident electromagnetic radiation at large angles of incidence without astigmatism, where the second mirror and the detector are not in the line of sight of hot plasma target.

A still other object of the present invention is to provide an exact definition of the requirements that must be satisfied for an application of these imaging schemes to imaging with x-rays and EUV radiation, namely:

First requirement: The centers of the two reflector spheres must be placed at one and the same point, called "O".

Second requirement: The two spherical reflectors and their Rowland circles must be arranged around a central circle, whose center is also at the same point "O" and whose radius RT must be: $RT = R_1 \cos(\theta_1) = R_2 \cos(\theta_2)$ where $R_1$, $R_2$, $\theta_1$, $\theta_2$ are the radii of curvature of the two spherical reflectors and the Bragg angles on the two reflectors, respectively.

Third requirement: If $0° < \theta_1 < 45°$ and if $45° < \theta_2 < 90°$, the rays between the two crystals or reflectors must fulfill the so called convergence/divergence condition:

$$-R_1 \cos(\theta_1) \cdot \tan(2\theta_1) = R_2 \cos(\theta_2) \cdot \tan(2\theta_2)$$

Fourth requirement: If $0° < \theta_1 < 45°$ and if $45° < \theta_2 < 90°$, the sum of the Bragg angles must be: $\theta_1 + \theta_2 = 90°$.

The present invention eliminates the astigmatism encountered in wide angle point-to-point imaging with electromagnetic radiation and ultrasound by using a matched pair of spherically bent reflectors, such as crystals, multilayer structures or minors. This invention is particularly adapted for use in the diagnosis of high energy plasmas by providing imaging schemes with large angles of incidence, which can replace the presently used imaging schemes of near-paraxial rays where expensive detectors and cameras currently must be placed in direct view of an exploding target and are thus at risk of being damaged by debris. In addition for use in detecting and measuring high energy radiation emitted by high temperature plasmas, this invention is also applicable for use with a very broad spectrum of electromagnetic radiation, such as microwaves, infrared and visible light, and UV and EUV radiation, and even to the imaging with ultrasound, if the aforementioned crystals are replaced by appropriate spherical minors. This invention is applicable for use with co-planar reflectors as well as with non-co-planar reflectors.

BRIEF DESCRIPTION OF THE DRAWINGS

The appended claims set forth those novel features which characterize the invention. However, the invention itself, as well as further objects and advantages thereof, will best be understood by reference to the following detailed description of a preferred embodiment taken in conjunction with the accompanying drawings, where like reference characters identify like elements throughout the various figures, in which:

DETAILED DESCRIPTION OF THE PREFERRED EMBODIMENTS

Figure 2A:
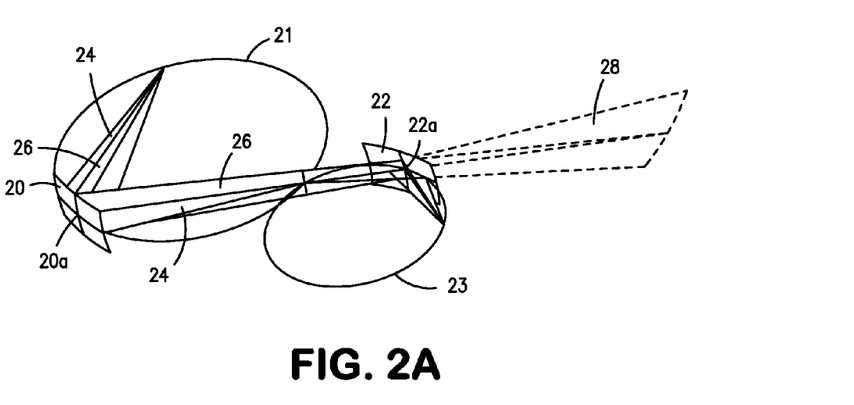
FIG. 2a is a simplified schematic diagram of an electromagnetic radiation as well as ultrasound imaging arrangement in accordance with one embodiment of the present invention incorporating a matched pair of spherical reflectors to eliminate astigmatism.
Figure 2B:
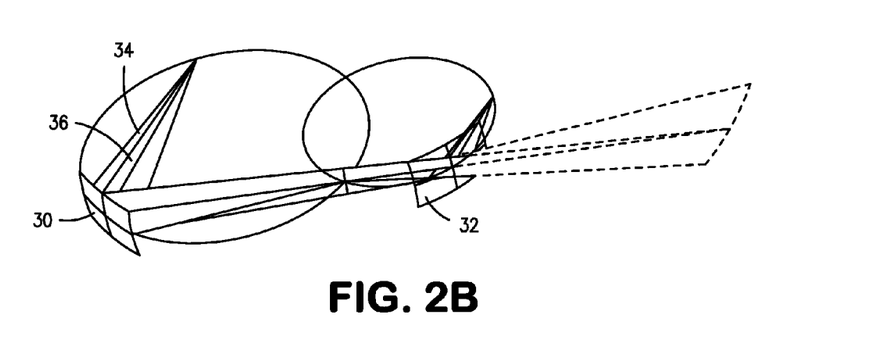
FIG. 2b is a simplified schematic diagram of an electromagnetic radiation as well as ultrasound imaging scheme in accordance with another embodiment of the present invention, including a matched pair of spherical crystals.
Figure 3:
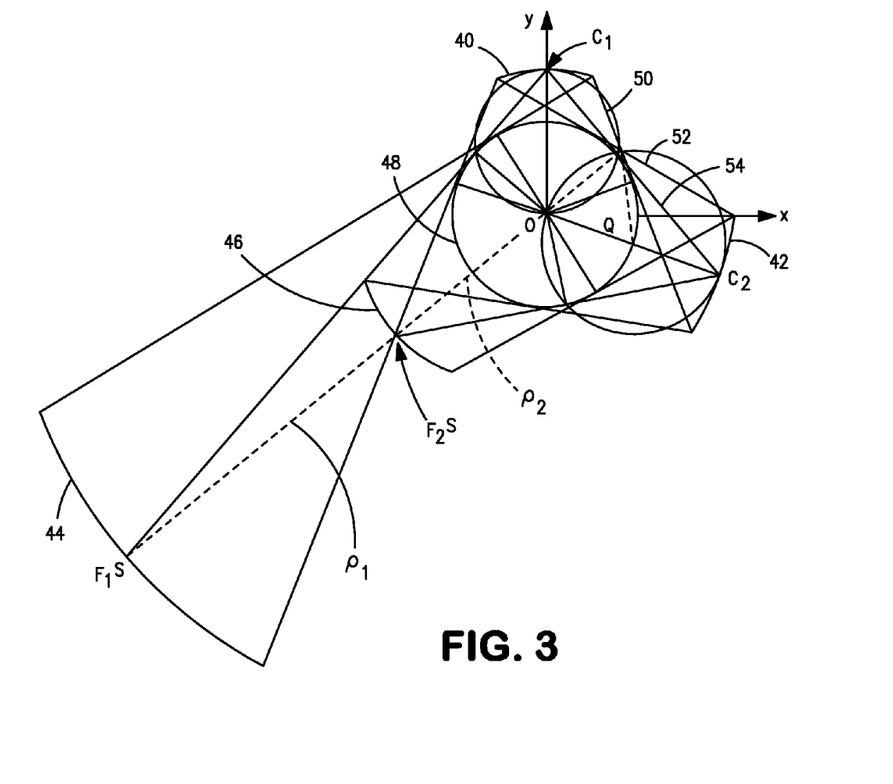
FIG. 3 is an electromagnetic radiation as well as ultrasound imaging arrangement particularly adapted for use in providing large magnification or large de-magnification of electromagnetic radiation images, where the Bragg angles on the two crystals are larger than 45° and the two sagittal ray images are real.
Figure 5:
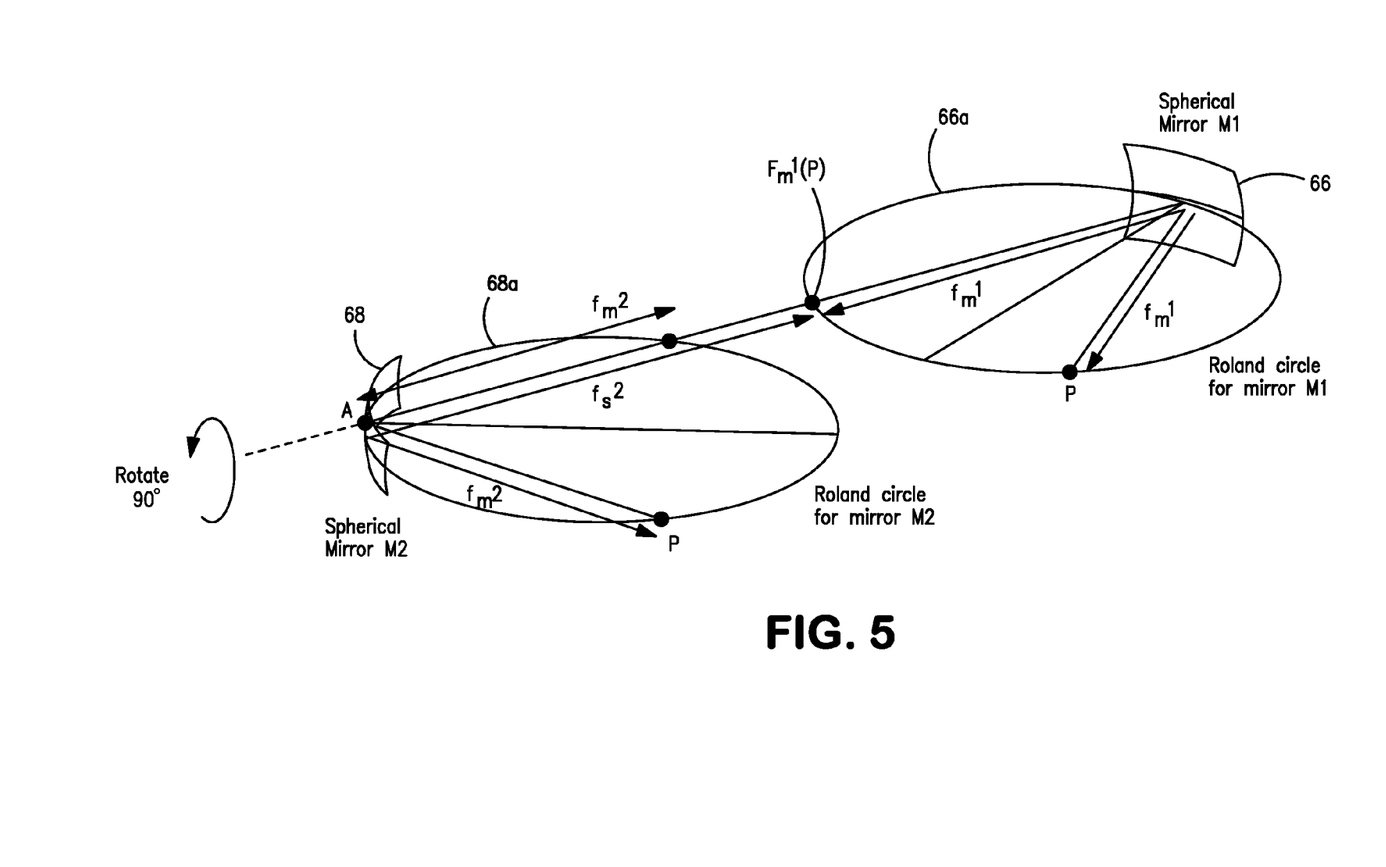
FIG. 5 illustrates the geometry for a pair of non-co-planar spherical reflectors in accordance with another embodiment of the present invention, where, for simplicity, the second reflector is shown prior to being rotated 90° about axis A-B to provide a three dimensional imaging capability.

It is well known that imaging systems with conventional lenses are restricted to the use of near-paraxial rays to avoid image distortions by spherical aberration and astigmatism. Spherical aberration and chromatic aberration, another imaging error of lenses, can be avoided by the use of spherical and parabolic mirrors, as is being demonstrated by the design of large minor telescopes, where the restrictions on the optical apertures and light intensity that exist for imaging schemes with lenses have been substantially relaxed. However, the astigmatic errors which occur for large angles of incidence are not eliminated by the use of spherical mirrors, as is illustrated in FIG. 1 for the special case of a point source on the Rowland circle discussed above. This case is of particular interest in the design and operation of the recently developed Johann-type X-ray imaging crystal spectrometers described in U.S. Pat. No. 6,259,763. For large angles of incidence, i.e. Bragg angles Θ that deviate significantly from 90°, two separate and mutually perpendicular line images of the point source on the Rowland circle 16 are formed by the meridional and sagittal rays 14, 12 at positions $F_m$ and $F_s$ as a result of the astigmatism at distances $$f_m = R \cdot \sin(\theta) \tag{1}$$

and $$f_s = -\frac{R \cdot \sin(\theta)}{\cos(2\theta)} \tag{2}$$

from the spherically bent reflector 10, where θ and R and are respectively the Bragg angle and radius of curvature of the crystal. Note that the diameter of the Rowland circle 16 is equal to the radius of curvature R of the mirror 10. According to equation (2), $f_s$ is positive for 45°<θ<90°, so that the reflected sagittal rays are convergent, forming a real image in front of the minor, and negative for 0°<θ<45°, meaning that the reflected sagittal rays are divergent and form a virtual image behind the mirror. For θ=45°, $f_s=\infty$, so that the reflected sagittal rays are parallel. The idea of the new imaging schemes of the present invention is to eliminate the astigmatic errors by a pair of properly matched, spherically bent crystals or spherically bent reflectors. The imaging schemes, shown in FIGS. 2a and 2b and in FIG. 5, represent the case, where one of the Bragg angles is in the range of 0°<θ≦45°, as for crystals 22 and 32, and where the other Bragg angle is in the range of 45°<θ<90°, as for crystals 20 and 30, whereas the imaging scheme, shown in FIG. 3, represents the case, where the Bragg angles on both spherical reflectors 40 and 42 are in the range 45°<θ<90°. These imaging schemes are applicable for a wide spectrum of the electromagnetic radiation and even ultrasound. However, with respect to the conditions that must be satisfied it is necessary to distinguish between x-rays and/or EUV radiation and other radiations, since for x-rays and EUV radiation also the Bragg condition must be fulfilled on both reflectors, where these reflectors would be spherically bent crystals or spherically bent multilayer structures, respectively. We first describe the necessary condition for the applications of these schemes to radiations other than x-rays or EUV radiation and consider the special requirements for x-rays and EUV radiation separately below in detail. For radiations other than x-rays or EUV radiation, the only requirement with respect to the imaging schemes, shown in FIGS. 2a and 2b and in FIG. 5, is that the rays between the two reflectors satisfy the so-called convergence/divergence condition:

$$f_s^1 = f_m^1 + f_m^2 + |f_s^2| \tag{5}$$

where $|f_s^2|$ must be used, since $f_s^2<0$. The condition of equation (5) can be inferred from FIG. 2a and ensures that the two real meridional images and the real and virtual sagittal images formed by the two crystals 20,22 appear at the same locations, so that the meridional and sagittal rays reflected from the two crystals have the same angles of convergence and divergence, respectively. Using equations (1) and (2), the condition of equation (5) can be rewritten as $$-R_1\cos(\theta_1)\cdot\tan(2\theta_1)=R_2\cos(\theta_2)\cdot\tan(2\theta_2) \qquad (6)$$

What follows is a detailed description of the conditions, which must be satisfied for the use of the imaging schemes with x-rays and EUV radiation, where the reflectors are spherically bent crystals or spherically bent multilayer structures, respectively. These conditions lead to two additional embodiments of the present invention, shown in FIG. 3 and FIG. 4, which may be employed for the diagnosis of laser-produced plasmas, the imaging of biological samples, using the highly monochromatic radiation from synchrotron light sources, and for lithography with EUV radiation.

Figure 4:
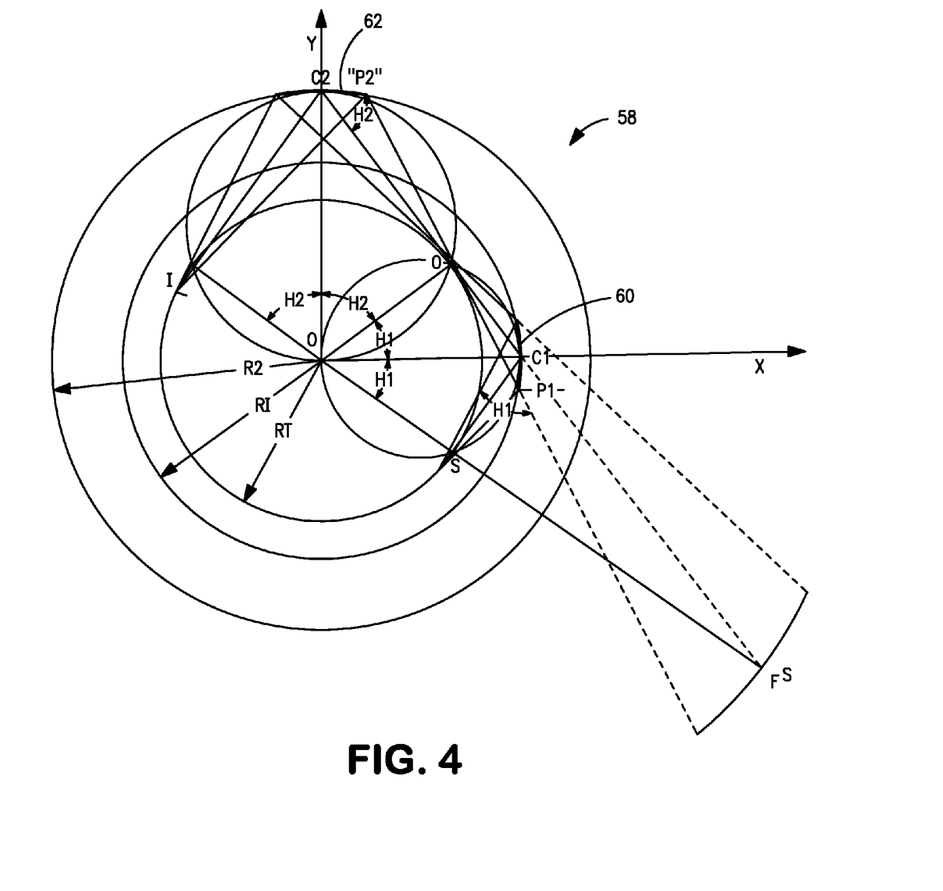
FIG. 4 is an electromagnetic radiation as well as ultrasound imaging arrangement in accordance with another embodiment of the present invention, where the first Bragg angle is 36.244° and the second Bragg angle is 53.756°, satisfying the condition, $\theta_1 + \theta_2 = 90°$, and where the sagittal ray image of a point source produced by the first crystal is a virtual image and only the sagittal ray image produced by the second crystal is real.

For the imaging with x-rays or EUV radiation, the Bragg condition $$\lambda=2d_1\sin(\theta_1)=2\,d_2\sin(\theta_2) \qquad (8)$$

must be simultaneously fulfilled on both reflectors of a crystal pair or a pair of multilayer structures, respectively. Here, $\lambda$ is the wavelength of the incident rays, and $d_1$, $d_2$ and $\theta_1$, $\theta_2$ are the 2d-spacings and Bragg angles for the two crystals or the two multilayer structures respectively. This condition leads to a specific experimental arrangement, where the two spherically bent reflectors, with their Rowland circles, are grouped around a central circle with the radius equal to $$RT=R_1\cos(\theta_1)=R_2\cos(\theta_2) \qquad (9)$$

such that the incident and reflected rays for both reflectors are tangent to this circle. Here, the center of the circle with radius RT and the centers of the two reflector spheres with radii $R_1$ and $R_2$ must be at the same point. This experimental arrangement is common to the two schemes described below and shown in FIGS. 3 and 4. These imaging arrangements are associated with the following two cases, which must be distinguished according to the values for the Bragg angles $\theta_1$ and $\theta_2$.

Case I: As shown in FIG. 3, $\theta_1>45°$ and $\theta_2>45°$. In this case, the sagittal images, produced by the two reflectors 40 and 42, are both real, and only the conditions of equations (8) and (9) must be satisfied.

Case II: As shown in FIG. 4, one of the Bragg angles is smaller and the other larger than 45°, e.g., $\theta_1<45°$ and $\theta_2>45°$. In this case, only the sagittal image produced by reflector 62 is real, whereas the sagittal image obtained from reflector 60 is a virtual image $F_s$, meaning that the sagittal rays reflected by reflector 60 are divergent and appear to emanate from a virtual focus behind the reflector. Therefore, an additional condition, the so-called convergence/divergence condition, $$R_1\cos(\theta_1)\cdot\tan(2\theta_1)=-R_2\cos(\theta_2)\cdot\tan(2\theta_2) \qquad (10)$$

which was already given as equation (6) above, must be satisfied for the rays between the two reflectors. Equation (10) is evidently different from equation (9). However, both conditions can be satisfied if $$\theta_1+\theta_2=90° \qquad (11)$$

since then $\tan(2\theta_1)=-\tan(2\theta_2)$.

We first consider the experimental arrangement which is associated with case I, where both Bragg angles are larger than 45°. FIG. 3 shows a schematic for the parameters: $\theta_1=50°$, $R_1=12.0$; $\theta_2=60°$, $R_2=15.4$. Here, the values for the radii of curvature for the two reflectors 40 and 42 were chosen to satisfy the condition of equation (9), so that $RT=R_1\cos(\theta_1)=R_2\cos(\theta_2)=7.7$. As shown in FIG. 3, the two reflectors 40, 42 and the corresponding Rowland circles 44 and 46, whose radii are equal to ½ the radius of the reflector curvature, are arranged around a central circle 48 with the radius RT, such that the rays between the two reflectors are tangent to this circle. In order to meet this requirement, the centers of this central circle 48 and the two reflector spheres must be at the same point, O, which is also the origin of the x,y-coordinate system, shown in FIG. 3. The size of the two reflectors 40, 42 is largely exaggerated to depict the Johann error, which is the deviation of the edge rays 50 and 52 from the central circle 48 with radius RT at the point Q, where the central ray 54 is tangent to this circle. As shown in FIG. 3, the Johann error is exactly the same for both reflectors. We also infer from FIG. 3 that the central points, $F_1^s$ and $F_2^s$, of the two sagittal images, which are associated with the two reflectors, fall on the same line (dashed line) through the point O at different locations; and by following the rays which connect corresponding points of the two sagittal images, we see that the sagittal image produced by crystal 40 represents a magnified image of the sagittal line focus of reflector 42. In an actual experiment, the object would be placed at $F_2^s$. The sagittal foci, $F_1^s$ and $F_2^s$, also lie on concentric circles with radii $\sigma_1$ and $\sigma_2$ about the point O. The magnification, $M_H$, in the horizontal plane, which is the drawing plane of FIG. 3, is therefore simply given by $$M_H=\frac{\rho_1}{\rho_2}. \qquad (12)$$

$\rho_1$ can be determined from the relation $$\rho_1+R_1\cos(\theta_1)=f_1^s\sin(2\theta_1), \qquad (13)$$

which is obtained from FIG. 3 by considering the triangle $C_1QF_1F_1^s$, where the internal angles at $C_1$, Q, and $F_1^s$ are $180°-2\theta_1$, $90°$, and $2\theta_1-90°$, respectively. Here, $$f_1^s=-\frac{R_1\sin(\theta_1)}{\cos(2\theta_1)}$$

is the distance of the sagittal focus $F_1^s$ from the center $C_1$ of reflector 40. Inserting this expression for $f_1^s$ into eq. (6), one obtains $$\rho_1=-\frac{R_1\cos(\theta_1)}{\cos(2\theta_1)} \qquad (14)$$

and by analogy $$\rho_2=-\frac{R_2\cos(\theta_2)}{\cos(2\theta_2)} \qquad (15)$$

so that the horizontal magnification $M_H$ is given by $$M_H=\frac{R_1\cos(\theta_1)\cdot\cos(2\theta_2)}{R_2\cos(\theta_2)\cdot\cos(2\theta_1)}=\frac{\cos(2\theta_2)}{\cos(2\theta_1)}, \qquad (16)$$

where we have used equation (9). In order to find the magnification, $M_V$, in the direction vertical to the drawing plane of FIG. 3, we imagine that the two reflectors are decoupled from each other and that the sagittal image, $F_1^s$, represents the image of an equivalent source, of at least the size of the Johann error, at the point Q. It then becomes clear that $M_V$ can be found by a rotation of the ray pattern about the y-axis, since respective to reflector 40 the ray pattern must have rotational symmetry about the normal to the reflector surface at $C_1$. After the relevant axis of rotation has thus been identified, we re-establish the actual ray pattern, which includes the incident and reflected rays from reflector 42, at the point Q and imagine that the whole ray pattern is being rotated about the y-axis. Since the axis of rotation (y-axis) passes through O, we see that by such a rotation of the ray pattern the point $C_2$ is moved to a point, '$C_2$', which is also on the reflector sphere with the radius $R_2$. The conditions of equations (8) and (9) are, therefore, always fulfilled during such a rotation. Thus, the magnification $M_V$ is given by $$M_v = \frac{x_1}{x_2} \quad (17)$$

where $x_1$ and $x_2$ are the x-coordinates of the points $F_1^s$ and $F_2^s$, respectively. Since the points $F_1^s$ and $F_2^s$ lie on the same line through the point O, at the distances $\rho_1$ and $\rho_2$ from O, it follows that the ratio of the x-coordinates must be equal to the ratio of $\rho_1$ and $\rho_2$, so that $$M_v = \frac{x_1}{x_2} = \frac{\rho_1}{\rho_2} = \frac{\cos(2\theta_2)}{\cos(2\theta_1)} = M_H \quad (18)$$

The magnification is therefore uniform and isotropic, i.e., independent of the direction, so that one obtains a magnified, undistorted image in all directions. This uniform magnification depends only on the Bragg angles $\theta_1$ and $\theta_2$ and is variable over a wide range. The magnification can be large if the Bragg angle $\theta_1$ is near 45°. We point out that in a real experimental setup, the reflector dimensions are much smaller than shown in FIG. 3, so that the rays which form the sagittal image at $F_1^s$ would not be blocked by a source which for the x-ray imaging of small samples would be placed at $F_2^s$. This imaging scheme may be employed for the x-ray imaging of biological samples, using the highly monochromatic radiation at synchrotron light sources. It also has an important application in EUV lithography, where it offers considerable simplifications or advantages over the presently used systems, if the spherically bent reflectors are replaced by appropriate spherical multilayer reflectors. For this application the mask would be placed at $F_1^s$, in order to obtain a de-magnified image at $F_2^s$. The de-magnification can be selected by choosing appropriate values for the Bragg angles $\theta_1$ and $\theta_2$. The main advantages for an application of this scheme to EUV lithography would be due to the fact that it provides non-astigmatic images with uniform and isotropic de-magnification and that only two reflectors are needed after the mask. It may also be important that with this scheme a two-dimensional image of the mask could be produced at once, so that a scanning process is not needed.

The imaging scheme, which is associated with case II, where in addition to the conditions of equations (8) and (9) also the conditions of equations (10) and (11) must be satisfied, is shown in FIG. 4 and is discussed below. This arrangement is shown in FIGS. 2a and 2b, where we stated that only the variant shown in FIG. 2b is usable for x rays. We also stated above that the Bragg conditions (on both crystals) would be strictly fulfilled only for the special pair of Bragg angles, $\theta_1=60°$ and $\theta_2=30°$, if the finite width of the rocking curve were neglected. This latter statement must now be replaced by the more general condition of equation (11), which offers a much wider choice of Bragg angle combinations for this imaging scheme.

Here we describe the design of a double-crystal spectrometer 58, which is associated with case II and satisfies the requirements of equations (8)-(11). The spectrometer 58 design is shown in FIG. 4 and is intended to be used for the observation of the spectra of helium-like argon in the wavelength range from 3.9494 Å to 3.9944 Å, which includes the helium-like lines w, x, y, and z and the associated dielectronic and inner-shell excited lithium-like satellites. The spectrometer 58 consists of two spherically bent crystals: a Highly Ordered Pyrolytic Graphite (HOPG) crystal 60 with a 2d-spacing of 6.702 Å and a 110-quartz crystal 62 with a 2d-spacing 4.91304 Å. The HOPG crystal 60 is a mosaic crystal with a mosaic spread that may vary between 0.4° and 0.8°. This crystal has a high reflectivity and a coarse spectral resolution. It is therefore used as the first crystal, which is irradiated by the source S. The 110-quartz crystal 62 has a high intrinsic resolution of 50 μrad rocking curve width and is used as the second crystal.

The conditions of equations (8)-(11) are exactly fulfilled for a certain wavelength $\lambda^*$, and the corresponding Bragg angles, $\theta_1^*$ and $\theta_2^*$, are determined by the Bragg condition $$\lambda^* = 2d_1 \sin(\theta_1^*) = 2d_2 \sin(\theta_2^*) = 2d_2 \sin(90° - \theta_1^*) \quad (19)$$

leading to $$\tan(\theta_1^*) = \frac{d_2}{d_1} \quad (20)$$

so that equation (19) and equation (20) yield the values: $\lambda^*=3.9624$ Å, $\theta_1^*=36.244°$, and $\theta_2^*=53.756°$, for which the spectrometer 58 is optimized. The wavelength $\lambda^*$ is well within the wavelength range of interest, which is spanned by the lines w and z at $\lambda_w=3.9494$ Å to $\lambda_z=3.9944$ Å. The corresponding Bragg angles, see Table 1, deviate from the optimal Bragg angles $\theta_1^*=36.244°$ and $\theta_2^*=53.756°$ by only a few tenths of a degree, which is smaller than the mosaic spread of the HOPG crystal 60. One should, therefore, suspect that this spectrometer will be applicable for the whole wavelength range of interest from $\lambda_w$ to $\lambda_z$.

TABLE 1

|  | $\theta_1$ | $\theta_2$ |
| --- | --- | --- |
| $\lambda_w = 3.9494$ Å | 36.106° | 53.500° |
| $\lambda^* = 3.9624$ Å | 36.244° | 53.756° |
| $\lambda_z = 3.9944$ Å | 36.584° | 54.392° |

We conclude this section with some additional remarks about the spectrometer 58 design shown in FIG. 4. The design is fully determined by the conditions of equations (8)-(11) if the lattice constants $d_1$ and $d_2$ of the two crystals and the parameters of the first crystal 60, namely, the width $W_1$, height $H_1$, and the radius of curvature $R_1$ are given. The origin O of the x,y-coordinate system in FIG. 4 is at the center of the two crystal spheres with the crystal curvature radii, $R_1$ and $R_2$, which is also the center of the circle with the radius RT, defined by equation (9). The x- and y-axes pass through $C_1$ and $C_2$, the central points on the two crystals, since the angle between the normals to the two crystals at C1 and C2 must be equal to $\theta_1+\theta_2=90°$. The points S and I denote the positions of a point source and its image, respectively. $F^s$ is the central point of the virtual sagittal line image, produced of a source at S by the first crystal 60, as well as the central point of the real sagittal line image that would be produced by the second crystal 62 of a source located at I. Thereby the convergence/divergence condition of equation (10) for the rays between the two crystals is satisfied. The symmetries of the ray pattern and the imaging properties of the meridional and sagittal rays can best be visualized by two rotations of the triangle IF$^s$C2. The first rotation of the triangle is executed in the drawing plane of FIG. 4 about a vertical axis through the point O. The second (subsequent) rotation of the triangle is then executed about an axis in the drawing plane of FIG. 4, which passes through the points I', O, and F$^{s'}$, where I', and F$^{s'}$ are the new positions of I, and F$^s$, respectively, after the first rotation. During the first rotation, the points C1 and C2 slide along the crystal surfaces to new positions "P$_1$" and "P$_2$", and the point Q slides on the circumference of the central circle with radius RT. Also, the line C1C2 is transformed into the line P1P2, which are both tangential to the central circle with radius RT—see FIG. 4. During the second rotation, the points C2 and C1 (and P$_1$ and P$_2$) remain on the crystal surfaces and move to new positions above or below the drawing plane of FIG. 4, such that the elevated lines of the triangles represent the sagittal rays. Since the points "P$_1$" and "P$_2$" are reached from the points C1 and C2 by a rigid rotation of the triangle, it is clear that the widths W$_1$ and W$_2$ of the two crystals are related by $$\frac{W_2}{W_1} = \frac{R_2}{R_1} = \frac{d_1}{d_2}, \quad (21)$$

where the last equation on the RHS of equation (13) follows from equations (9), (11), and (20).

The heights H$_1$ and H$_2$ of the two crystals are given by $$\frac{H_2}{H_1} = \frac{f_2^s}{|f_1^s|} \quad (22)$$

where $$f_{1,2}^s = -\frac{R_{1,2}\sin(\theta_{1,2})}{\cos(2\theta_{1,2})}$$

represents the distance of the sagittal focus F$^s$ from C$_1$ and C$_2$, respectively. Using again equations (9), (11), and (21), one obtains $$\frac{H_2}{H_1} = \frac{R_2}{R_1} \cdot \frac{1}{\tan(\theta_1)} = \frac{R_2^2}{R_1^2} = \frac{d_1^2}{d_2^2} \quad (23)$$

The magnification M$_V$ of the imaging scheme in a direction perpendicular to the drawing plane is obtained by considering a rotation of the ray pattern about the y-axis, whereby the points I and S are moved in opposite directions to positions above and below the drawing plane, so that $$M_v = \frac{x_2}{x_1} = \frac{RT\sin(\theta_2)}{RT\cos(\theta_1)} = 1 \quad (24)$$

where x$_1$ and x$_2$ are the abscissas of points S and I, respectively, and where we have again used equation (11).

The previously described embodiments of the invention are directed to the situation where the first and second reflectors are co-planar. Two other embodiments of this invention address arrangements where not all the reflectors are co-planar:

The first arrangement consists of two crystal (or reflector) pairs in series, where a reflector pair as shown in FIG. 2 and FIG. 4 is followed by a similar reflector pair that uses the image from the first reflector pair as the source. Since the image obtained from the first reflector pair is produced by rays that form a circular cone, the plane of the second reflector pair—which uses the rays emanating form the image of the first reflector pair as input—can be rotated about the axis of this circular cone by an arbitrary angle.

The second arrangement consists of only two reflectors (instead of two reflector pairs in series), where the planes of the two Rowland circles are rotated by 90° to one another. This scheme, which is shown in FIG. 5, is not applicable to x-rays and EUV radiation, since the Bragg conditions cannot be simultaneously fulfilled on both reflectors.

FIG. 5 illustrates the geometry of the embodiment of the invention. A fan of meridional rays originating from point P lies in the plane of the first Rowland circle 66a of the first mirror 66. The image is formed at point P' which lies on the second Rowland circle 68a of the second mirror 68. For clarity, the configuration of the first and second minors 66 and 68 in FIG. 5 is illustrated before the second minor 68 is rotated 90° about the axis A-B. Following the rotation of the second minor 68, meridional rays in first minor 66 frame of reference become sagittal rays in the frame of second mirror 68, and conversely sagittal rays in the first mirror frame of reference become meridional rays in the frame of the second minor. We impose the constraint that both mirrors 66 and 68 have a real sagittal focus point, i.e. $f_{s1}>0$ and $f_{s2}>0$, which in turn requires $45°<\theta_1<90°$ and $45°<\theta_2<90°$.

Meridional rays from the object P on the Rowland circle 66a of spherical mirror 66 are focused to point $F_{m1}(P)$ which is also located on the Rowland circle 66a. The second minor 68 is positioned a distance d from the first mirror 66, where $$d=f_{m1}+f_{s2} \quad (25)$$

which ensures that the focal point $F_{m1}(P)$ is located at a distance $f_{s2}$ from the second minor 68. Thus, the point $F_{m1}(P)$ lies at the sagittal focal point of the second mirror 68, thereby ensuring point-to-point focusing of meridional rays from the object P.

The minor configuration must also provide for point-to-point imaging of sagittal rays from the object P. If the first minor 66 has height h$_1$, then a bundle of rays that originates at the object P will, upon striking the second mirror 68, have a height given by $h=h_1(d-f_{s1})/f_{s1}$. Because the second minor 68 is rotated 90 degrees, the height h defines the width of the ray bundle w$_2$ in the frame of reference of the second minor 68, $$w_2 = h_1\left(\frac{d-f_{s1}}{f_{s1}}\right) \quad (26)$$

The sagittal rays from the first minor 66 converge with a vertical half-angle β given by $\tan\beta=(h_1/2)/f_{s1}$. To ensure point-to-point imaging, we require that this angle be the same as the diverging angle in the meridional frame of the second minor 68, $\tan\alpha = (w_2/2)/f_{m2}$, i.e.

$$\frac{h_1}{f_{s1}} = \frac{w_2}{f_{m2}}. \quad (27)$$

Equations 26 and 27 can be solved, yielding $$f_{s2}-f_{s1}=f_{m2}-f_{m1} \quad (28)$$

Equations 25 and 28 define the relationships among the minor's focal lengths that ensure point-to-point imaging in a configuration with perpendicular Rowland circles.

In summary, the present invention contemplates electromagnetic or extreme ultraviolet imaging using a pair of spherically bent reflectors where the respective Rowland circles of the reflectors are arranged either co-planar to provide two dimensional point-to-point imaging or non-co-planar to provide three dimensional point-to-point imaging. Both approaches provide high quality imaging even at large angles of incidence without astigmatism. In the non-co-planar embodiments the planes of the two Rowland circles can be rotated to virtually any angle. Pairs of reflectors, which may be minors or crystals, may be arranged in series, since the image of a point source obtained from a pair of spherical reflectors is formed by a circular cone of rays, so that the plane of the Rowland circles of the following reflector pair can be rotated about the axis of this cone by an arbitrary angle. Therefore, by using plural crystal pairs in series in accordance with this invention, it is possible to establish almost any light path and still obtain the benefit of non-astigmatic point-to-point imaging.

While particular embodiments of the present invention have been shown and described, it will be obvious to those skilled in the relevant arts that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

We claim:

1. Apparatus for forming an image of an object using electromagnetic radiation including microwaves, infrared and visible as well as ultrasound, said apparatus comprising:
a first spherical reflector having a first Bragg angle $\theta_1$, a first real saggital focal length $f_{s1}>0$, a first real meridional focal length $f_{m1}>0$, and a first Rowland circle having a radius $R_1$, wherein the object is positioned on said first Rowland circle; and
a second spherical reflector having a second Bragg angle $\theta_2$, a second virtual sagittal focal length $f_{s2}<0$, a second real meridional focal length $f_{m2}>0$, and a second Rowland circle having a radius $R_2$, wherein the image of the object is positioned on said second Rowland circle and said first and second Rowland circles are co-planar;
wherein $f_{s1}=f_{m1}+f_{m2}+|f_{s2}|$.

2. Apparatus for forming an image of an object using x-ray or EUV electromagnetic radiation, said apparatus comprising:
a first spherical reflector having a first Bragg angle $\theta_1$, a first real sagittal focal length $f_{s1}>0$, and a first real meridional focal point length $f_{m1}>0$, and a first Rowland circle, wherein the object is positioned on said first Rowland circle; and
a second spherical reflector having a second Bragg angle $\theta_2$, a second real sagittal focal length $f_{s2}<0$, a second real meridional focal length $f_{m2}>0$, and a second Rowland circle, wherein the image is positioned on said second Rowland circle and said first and second Rowland circles are co-planar;
wherein $f_{s1}=f_{m1}+f_{m2}+|f_{s2}|$.
and wherein the centers of said first an second spherical reflectors are co-located at a point O and wherein the object and its image are located on a third circle whose center is at point O and whose radius is RT, where $$RT = R_1 \cos(\theta_1) = R_2 \cos(\theta_2)$$

and wherein $\theta_1+\theta_2=90°$.

3. Apparatus for forming an image of an object using electromagnetic radiation including microwaves, infrared and visible as well as ultrasound, said apparatus comprising:
a first spherical reflector having a radius of curvature $R_1$ and a first Bragg angle $\theta_1$, a first sagittal focal length $f_{s1}>0$, a first real meridional focal length $f_{m1}>0$, and wherein the object is positioned at the sagittal focus $f_{s1}$; and
a second spherical reflector having a radius of curvature $R_2$ and a second Bragg angle $\theta_2$, a second sagittal focal length $f_{s2}>0$, a second meridional focal length $f_{m2}>0$, and wherein the image of the object is positioned at the second sagittal focus $f_{s2}$ and said first and second Rowland circles are co-planar;
wherein the centers of the said first and second spherical reflectors are co-located at a point "O".

4. Apparatus, for forming an image of an object using x-rays or EUV radiation, said apparatus comprising:
a first spherical reflector having a radius of curvature $R_1$ and a first Bragg angle $\theta_1$, a first sagittal focal length $f_{s1}>0$ and a first meridional focal length $f_{m1}$, and wherein the object is positioned at the first sagittal focus $f_{s1}$; and
a second spherical reflector having a radius of curvature $R_2$ and a second Bragg angle $\theta_2$, a second sagittal focal length $f_{s2}>0$, a second meridional focal length $f_{m2}>0$, and wherein the image of the object is positioned at the second sagittal focus $f_{s2}$ and said first and second Rowland circles are co-planar;
wherein the centers of the said first and second spherical reflectors are co-located at a point "O" and said first and second reflectors and said first and second Rowland circles are arranged around a third central circle, whose center is at the same point "O" and whose radius RT is:

$$RT = R_1 \cos(\theta_1) = R_2 \cos(\theta_2).$$

5. Apparatus for forming an image of an object using electromagnetic radiation or ultrasound, said apparatus comprising:
a first spherical reflector having a radius of curvature $R_1$ and a first Bragg angle $\theta_1$, a first sagittal focal length $f_{s1}>0$ and a first meridional focal length $f_{m1}$, and wherein the object is positioned on the first said Rowland circle; and
a second spherical reflector having a radius of curvature $R_2$ and a second Bragg angle $\theta_2$, a second sagittal focal length $f_{s2}<0$, a second meridional focal length $f_{m2}>0$, and wherein the image of the object is positioned on said second Rowland circle and said first and second Rowland circles are co-planar;

wherein $$f_{s1} = f_{m1} + f_{m2} + |f_{s2}|$$

and the centers of said first an second spherical reflectors are co-located at a point "O" and said first and second reflectors are disposed about a third circle having a center located at point "O" and having a radius RT, where $$RT = R_1 \cos(\theta_1) = R_2 \cos(\theta_2),$$

and wherein all of the rays forming an image of the object are tangential to said third circle;

and wherein if $0° < \theta_1 < 45°$ and $45° < \theta_2 < 90°$, the convergence and divergence of the rays between the said first and second spherical reflectors is such that $$-R_1 \cos(\theta_1) \cdot \tan(2\theta_1) = R_2 \cos(\theta_2) \cdot \tan(2\theta_2)$$

and wherein for x-rays and EUV radiation, if $45° < \theta_1 < 90°$ and $0° < \theta_2 < 45°$, then $\theta_1 + \theta_2 = 90°$.

6. Apparatus for forming an image of an object using electromagnetic radiation or ultrasound, said apparatus comprising:

first and second spherical reflectors having respective first and second Rowland circles, wherein said first and second Rowland circles are co-planar and wherein an image is produced on said second Rowland circle of an object located on said first Rowland circle; and third and fourth of spherical reflectors having respective third and fourth Rowland circles, wherein said third and fourth Rowland circles are co-planar, and wherein said third and fourth reflectors are arranged in pairs with said first and second reflectors;

wherein the planes of said third and fourth Rowland circles are rotationally displaced relative to the planes of said first and second Rowland circles; and wherein said first and second reflectors form an first image of an object and wherein said third and fourth reflectors form a second image of said first image and wherein said object and said second image are non-coplanar.

7. Apparatus for forming an image of an object using electromagnetic radiation or ultrasound, said apparatus comprising:

a first spherical reflector having a first sagittal focal length $f_{s1} > 0$, a first meridional focal length $f_{m1} > 0$, and a first Rowland circle, wherein the object is positioned on said first Rowland circle; and a second spherical reflector having a second sagittal focal length $f_{s2} > 0$, a second meridional focal length $f_{m2} > 0$, and a second Rowland circle, wherein an image of the object is positioned on said second Rowland circle and wherein said first and said second Rowland circles are perpendicular to one another; and wherein said second spherical reflector is located in the plane of the said first Rowland circle at a position such that a light ray from the object reflected at the center of said first spherical reflector is incident on said second spherical reflector; wherein the distance d between the first and second spherical reflectors satisfies $d = f_{m1} + f_{s2}$ and wherein the sagittal and meridional focal lengths of the first and second spherical reflectors satisfy $f_{s2} - f_{s1} = f_{m2} - f_{m1}$.

* * * * *